(12) United States Patent
Lui et al.

(10) Patent No.: US 10,822,631 B2
(45) Date of Patent: Nov. 3, 2020

(54) DEACETOXYCEPHALOSPORIN C HYDROXYLASE MUTANTS, DNA ENCODING THE MUTANTS, METHOD FOR UTILIZING THE MUTANTS AND APPLICATION THEREOF

(71) Applicant: BioRight Worldwide Co., Ltd., Road Town (VG)

(72) Inventors: Yuk Sun Lui, Hong Kong (CN); Shiu Ming Cheng, Hong Kong (CN); Yuen Wing Chow, Hong Kong (CN); Yau Lung Siu, Hong Kong (CN); Jun Wang, Hong Kong (CN)

(73) Assignee: BioRight Worldwide Co., Ltd., Tortola (VG)

( * ) Notice: Subject to any disclaimer, the term of this patent is extended or adjusted under 35 U.S.C. 154(b) by 74 days.

(21) Appl. No.: 16/310,518

(22) PCT Filed: Jun. 1, 2017

(86) PCT No.: PCT/CN2017/086843
§ 371 (c)(1),
(2) Date: Dec. 17, 2018

(87) PCT Pub. No.: WO2018/001034
PCT Pub. Date: Jan. 4, 2018

(65) Prior Publication Data
US 2019/0330673 A1    Oct. 31, 2019

(30) Foreign Application Priority Data
Jul. 1, 2016 (CN) .......................... 2016 1 0516090

(51) Int. Cl.
*C12P 35/02* (2006.01)
*C12N 15/52* (2006.01)

(52) U.S. Cl.
CPC .............. *C12P 35/02* (2013.01); *C12N 15/52* (2013.01); *C12Y 114/11026* (2013.01)

(58) Field of Classification Search
CPC ... C12N 15/52; C12P 35/02; C12Y 114/11026
See application file for complete search history.

(56) References Cited

U.S. PATENT DOCUMENTS 6,180,361 B1   1/2001   Ingolia et al.
9,404,139 B2   8/2016   Durairaaj et al.

FOREIGN PATENT DOCUMENTS

| CN | 104364376 A | 2/2015 |
|---|---|---|
| EP | 0465189 A2 | 1/1992 |
| WO | 2008107782 A2 | 9/2008 |
| WO | 2013105030 A1 | 7/2013 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Lloyd et al., "Controlling the Substrate Selectivity of Deacetoxycephalosporin/deacetylcephalosporin C Synthase," The Journal of Biological Chemistry, 2004, pp. 15420-15426, vol. 279:15.
Han et al., "Research progress on biosynthesis and regulatory mechanisms of cephamycin C in *Streptomyces clavuligeru*," Chinese Journal of Antiobiotics, 2015, pp. 561-569, vol. 40:8.
Wei et al., "Directed Evolution of *Streptomyces clavuligerus* Deacetoxycephalosporin C Synthase for Enhancement of Penicillin G Expansion," Applied and Environmental Microbiology, 2005, pp. 8873-8880, vol. 71:12.
Wu et al., "C-terminus Mutations of Acremonium chrysogenum deacetoxy/deacetylcephalosporin C synthase with improved activity towards penicillin analogs," FEMS Microbiology Letters, 2005, pp. 103-110, vol. 246.

* cited by examiner

*Primary Examiner* — Ganapathirama Raghu
(74) *Attorney, Agent, or Firm* — The Webb Law Firm

(57) ABSTRACT

This invention provides deacetoxycephalosporin C hydroxylase mutants, their encoding DNA sequences, the methods to utilize them and their application. The deacetoxycephalosporin C hydroxylase mutants are characterized by at least one amino acid mutation at residue position selected from Glycine at position 29, Alanine at position 40, Glycine at position 41, Arginine at position 182 and Threonine at position 272, based on the amino acid sequence shown in SEQ ID NO.:2 as reference sequence, and wherein the deacetoxycephalosporin C hydroxylase mutant has at least 10% increase in activity and at least 150% increase in thermostability compared to wild-type deacetoxycephalosporin C hydroxylase. The deacetoxycephalosporin C hydroxylase mutants in this invention have increased activity and thermostability, allowing them to be more commercially and industrially viable.

14 Claims, No Drawings
Specification includes a Sequence Listing.

SEQUENCE LISTING

```
<160> NUMBER OF SEQ ID NOS: 28

<210> SEQ ID NO 1
<211> LENGTH: 957
<212> TYPE: DNA
<213> ORGANISM: Streptomyces clavuligerus

<400> SEQUENCE: 1
atggcagata ccccggtgcc gattttcaac ctggcagctc tgcgtgaagg tgccgaccaa      60
gaaaaatttc gcgaatgtgt gaccggcatg ggtgttttct atctgacggg ctacggtgca     120
ggcgataaag accaccgtct ggccaccgat acggcaatgg acttttttcgc taatggtacc    180 gaagcggaaa aagcggccgt caccacggat gtgccgacga tgcgtcgcgg ctattctgct    240
ctggaagcgg aaagtaccgc ccaggttacc cgcaccggta gctatacgga ttacagtatg    300
tccttttcaa tgggcatttc cggtaacgtt tttccgtcac cggaattcga acgtgtctgg    360
accgaatatt tcgataaact gtacgcagct gcgcaagaaa ccgcacgtct ggttctgacg    420
gcatctggcg gttatgatgc tgaaatcgtc ggtagtctgg acgaactgct ggatgcggac    480
ccggttctgc gtctgcgcta ttttccggaa gttccggaac atcgttcggc agaacacgaa    540
ccgcgtcgta tggcaccgca ttacgatctg agcattatca cctttattca ccagacgccg    600
tgcgcaaatg gcttcgtctc cctgcaagct gaaatcggcg tgaactggt gtcactgccg    660 gtggttgaag atgccgtcgt ggttatgtgt ggtgctatgg caccgctggc aacccagggt    720
gctctgccgg caccgcgtca tcacgtgcgc tcgccgggtg ccggtatgcg tgaaggtagc    780
gatcgcacca gctctgtttt ttttctgcgt ccgacgaccg acttttcgtt cagcgtggcc    840
aaagcacgca gctatggcct ggcagttgat ctggacatgg aaaccgcgac gtttggtgat    900
tggatcggca ccaactacgt tacgatgcat gcaaaaaatg aaccgcaggc gggctaa      957
```

-continued

```
<210> SEQ ID NO 2
<211> LENGTH: 318
<212> TYPE: PRT
<213> ORGANISM: Streptomyces clavuligerus

<400> SEQUENCE: 2

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr Gly Met Gly Val
            20                  25                  30

Phe Tyr Leu Thr Gly Tyr Gly Ala Gly Asp Lys Asp His Arg Leu Ala
        35                  40                  45

Thr Asp Thr Ala Met Asp Phe Phe Ala Asn Gly Thr Glu Ala Glu Lys
    50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
    130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Glu Leu Val Ser Leu Pro Val Val Glu Asp
    210                 215                 220

Ala Val Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Thr
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
    290                 295                 300

Asn Tyr Val Thr Met His Ala Lys Asn Glu Pro Gln Ala Gly
305                 310                 315

<210> SEQ ID NO 3
<211> LENGTH: 318
<212> TYPE: PRT
<213> ORGANISM: Artificial Sequence
<220> FEATURE:
<223> OTHER INFORMATION: HD-G29H

<400> SEQUENCE: 3

Met Ala Asp Thr Pro Val Pro Ile Phe Asn Leu Ala Ala Leu Arg Glu
1               5                   10                  15
```

```
Gly Ala Asp Gln Glu Lys Phe Arg Glu Cys Val Thr His Met Gly Val
            20                  25                  30

Phe Tyr Leu Thr Gly Tyr Gly Ala Gly Asp Lys Asp His Arg Leu Ala
            35                  40                  45

Thr Asp Thr Ala Met Asp Phe Phe Ala Asn Gly Thr Glu Ala Glu Lys
50                      55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
                100                 105                 110

Ser Pro Glu Phe Glu Arg Val Trp Thr Glu Tyr Phe Asp Lys Leu Tyr
            115                 120                 125

Ala Ala Ala Gln Glu Thr Ala Arg Leu Val Leu Thr Ala Ser Gly Gly
            130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
                180                 185                 190

Ile Thr Phe Ile His Gln Thr Pro Cys Ala Asn Gly Phe Val Ser Leu
            195                 200                 205

Gln Ala Glu Ile Gly Gly Leu Val Ser Leu Pro Val Val Glu Asp
            210                 215                 220

Ala Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Thr
            260                 265                 270

Thr Asp Phe Ser Phe Ser Val Ala Lys Ala Arg Ser Tyr Gly Leu Ala
            275                 280                 285

Val Asp Leu Asp Met Glu Thr Ala Thr Phe Gly Asp Trp Ile Gly Thr
            290                 295                 300

Asn Tyr Val Thr Met His Ala Lys Asn Glu Pro Gln Ala Gly
305                 310                 315

<210> SEQ ID NO 4
<211> LENGTH: 318
<212> TYPE: PRT
<213> ORGANISM: Artificial Sequence
<220> FEATURE:
<223> OTHER INFORMATION: HD-A40L

<400> SEQUENCE: 4

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr Gly Met Gly Val
            20                  25                  30

Phe Tyr Leu Thr Gly Tyr Gly Leu Gly Asp Lys Asp His Arg Leu Ala
            35                  40                  45

Thr Asp Thr Ala Met Asp Phe Phe Ala Asn Gly Thr Glu Ala Glu Lys
50                      55                  60
```

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Glu Leu Val Ser Leu Pro Val Val Glu Asp
210                 215                 220

Ala Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Thr
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
290                 295                 300

Asn Tyr Val Thr Met His Ala Lys Asn Glu Pro Gln Ala Gly
305                 310                 315

<210> SEQ ID NO 5
<211> LENGTH: 318
<212> TYPE: PRT
<213> ORGANISM: Artificial Sequence
<220> FEATURE:
<223> OTHER INFORMATION: HD-G41T

<400> SEQUENCE: 5

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr Gly Met Gly Val
                20                  25                  30

Phe Tyr Leu Thr Gly Tyr Gly Ala Thr Asp Lys Asp His Arg Leu Ala
            35                  40                  45

Thr Asp Thr Ala Met Asp Phe Phe Ala Asn Gly Thr Glu Ala Glu Lys
        50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
            115                 120                 125

Ala Ala Ala Gln Glu Thr Ala Arg Leu Val Leu Thr Ala Ser Gly Gly
        130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Glu Leu Val Ser Leu Pro Val Val Glu Asp
210                 215                 220

Ala Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Thr
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
290                 295                 300

Asn Tyr Val Thr Met His Ala Lys Asn Glu Pro Gln Ala Gly
305                 310                 315

<210> SEQ ID NO 6
<211> LENGTH: 318
<212> TYPE: PRT
<213> ORGANISM: Artificial Sequence
<220> FEATURE:
<223> OTHER INFORMATION: HD-R182D

<400> SEQUENCE: 6

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr Gly Met Gly Val
            20                  25                  30

Phe Tyr Leu Thr Gly Tyr Gly Ala Gly Asp Lys Asp His Arg Leu Ala
        35                  40                  45

Thr Asp Thr Ala Met Asp Phe Phe Ala Asn Gly Thr Glu Ala Glu Lys
    50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
    130                 135                 140

Tyr Asp Ala Glu Ile Val Gly Ser Leu Asp Glu Leu Leu Asp Ala Asp
145                 150                 155                 160

```
Pro Val Leu Arg Leu Arg Tyr Phe Pro Glu Val Pro Glu His Arg Ser
                165                 170                 175

Ala Glu His Glu Pro Asp Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Leu Val Ser Leu Pro Val Val Glu Asp
    210                 215                 220

Ala Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Thr
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
    290                 295                 300

Asn Tyr Val Thr Met His Ala Lys Asn Glu Pro Gln Ala Gly
305                 310                 315

<210> SEQ ID NO 7
<211> LENGTH: 318
<212> TYPE: PRT
<213> ORGANISM: Artificial Sequence
<220> FEATURE:
<223> OTHER INFORMATION: HD-T272R

<400> SEQUENCE: 7

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr Gly Met Gly Val
            20                  25                  30

Phe Tyr Leu Thr Gly Tyr Gly Ala Gly Asp Lys Asp His Arg Leu Ala
        35                  40                  45

Thr Asp Thr Ala Met Asp Phe Phe Ala Asn Gly Thr Glu Ala Glu Lys
    50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
    130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205
```

Gln Ala Glu Ile Gly Gly Glu Leu Val Ser Leu Pro Val Val Glu Asp
    210                 215                 220

Ala Val Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
            245                 250                 255

Arg Glu Gly Ser Asp Arg Thr Ser Ser Val Phe Phe Leu Arg Pro Arg
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
    290                 295                 300

Asn Tyr Val Thr Met His Ala Lys Asn Glu Pro Gln Ala Gly
305                 310                 315

<210> SEQ ID NO 8
<211> LENGTH: 318
<212> TYPE: PRT
<213> ORGANISM: Artificial Sequence
<220> FEATURE:
<223> OTHER INFORMATION: HD-29H41T

<400> SEQUENCE: 8

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr His Met Gly Val
            20                  25                  30

Phe Tyr Leu Thr Gly Tyr Gly Ala Thr Asp Lys Asp His Arg Leu Ala
        35                  40                  45

Thr Asp Thr Ala Met Asp Phe Phe Ala Asn Gly Thr Glu Ala Glu Lys
    50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
    130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Glu Leu Val Ser Leu Pro Val Val Glu Asp
    210                 215                 220

Ala Val Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
            245                 250                 255

Arg Glu Gly Ser Asp Arg Thr Ser Ser Val Phe Phe Leu Arg Pro Thr
                260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
290                 295                 300

Asn Tyr Val Thr Met His Ala Lys Asn Glu Pro Gln Ala Gly
305                 310                 315

<210> SEQ ID NO 9
<211> LENGTH: 318
<212> TYPE: PRT
<213> ORGANISM: Artificial Sequence
<220> FEATURE:
<223> OTHER INFORMATION: Sp3

<400> SEQUENCE: 9

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr His Met Gly Val
            20                  25                  30

Phe Tyr Leu Thr Gly Tyr Gly Ala Thr Asp Lys Asp His Arg Leu Ala
        35                  40                  45

Thr Asp Thr Ala Met Asp Phe Phe Ala Asn Gly Thr Glu Ala Glu Lys
    50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
    130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Glu Leu Val Ser Leu Pro Val Val Glu Asp
    210                 215                 220

Ala Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Arg
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
290                 295                 300

```
Asn Tyr Val Thr Met His Ala Lys Asn Glu Pro Gln Ala Gly
305                 310                 315
```

```
<210> SEQ ID NO 10
<211> LENGTH: 318
<212> TYPE: PRT
<213> ORGANISM: Artificial Sequence
<220> FEATURE:
<223> OTHER INFORMATION: Sp4

<400> SEQUENCE: 10

Met Ala Asp Thr Pro Val Pro Ile Phe Asn Leu Ala Ala Leu Arg Glu
1               5                   10                  15

Gly Ala Asp Gln Glu Lys Phe Arg Glu Cys Val Thr His Met Gly Val
                20                  25                  30

Phe Tyr Leu Thr Gly Tyr Gly Leu Thr Asp Lys Asp His Arg Leu Ala
            35                  40                  45

Thr Asp Thr Ala Met Asp Phe Phe Ala Asn Gly Thr Glu Ala Glu Lys
        50                  55                  60

Ala Ala Val Thr Thr Asp Val Pro Thr Met Arg Arg Gly Tyr Ser Ala
65                  70                  75                  80

Leu Glu Ala Glu Ser Thr Ala Gln Val Thr Arg Thr Gly Ser Tyr Thr
                85                  90                  95

Asp Tyr Ser Met Ser Phe Ser Met Gly Ile Ser Gly Asn Val Phe Pro
            100                 105                 110

Ser Pro Glu Phe Glu Arg Val Trp Thr Glu Tyr Phe Asp Lys Leu Tyr
        115                 120                 125

Ala Ala Ala Gln Glu Thr Ala Arg Leu Val Leu Thr Ala Ser Gly Gly
    130                 135                 140

Tyr Asp Ala Glu Ile Val Gly Ser Leu Asp Glu Leu Leu Asp Ala Asp
145                 150                 155                 160

Pro Val Leu Arg Leu Arg Tyr Phe Pro Glu Val Pro Glu His Arg Ser
                165                 170                 175

Ala Glu His Glu Pro Arg Arg Met Ala Pro His Tyr Asp Leu Ser Ile
            180                 185                 190

Ile Thr Phe Ile His Gln Thr Pro Cys Ala Asn Gly Phe Val Ser Leu
        195                 200                 205

Gln Ala Glu Ile Gly Gly Glu Leu Val Ser Leu Pro Val Val Glu Asp
    210                 215                 220

Ala Val Val Met Cys Gly Ala Met Ala Pro Leu Ala Thr Gln Gly
225                 230                 235                 240

Ala Leu Pro Ala Pro Arg His His Val Arg Ser Pro Gly Ala Gly Met
                245                 250                 255

Arg Glu Gly Ser Asp Arg Thr Ser Ser Val Phe Phe Leu Arg Pro Arg
            260                 265                 270

Thr Asp Phe Ser Phe Ser Val Ala Lys Ala Arg Ser Tyr Gly Leu Ala
        275                 280                 285

Val Asp Leu Asp Met Glu Thr Ala Thr Phe Gly Asp Trp Ile Gly Thr
    290                 295                 300

Asn Tyr Val Thr Met His Ala Lys Asn Glu Pro Gln Ala Gly
305                 310                 315
```

```
<210> SEQ ID NO 11
<211> LENGTH: 318
<212> TYPE: PRT
<213> ORGANISM: Artificial Sequence
```

<220> FEATURE:
<223> OTHER INFORMATION: Sp5

<400> SEQUENCE: 11

| Met | Ala | Asp | Thr | Pro | Val | Pro | Ile | Phe | Asn | Leu | Ala | Ala | Leu | Arg | Glu |
|---|---|---|---|---|---|---|---|---|---|---|---|---|---|---|---|
| 1 | | | | 5 | | | | | 10 | | | | | 15 | |

| Gly | Ala | Asp | Gln | Glu | Lys | Phe | Arg | Glu | Cys | Val | Thr | His | Met | Gly | Val |
|---|---|---|---|---|---|---|---|---|---|---|---|---|---|---|---|
| | | | 20 | | | | | 25 | | | | | 30 | | |

| Phe | Tyr | Leu | Thr | Gly | Tyr | Gly | Leu | Thr | Asp | Lys | Asp | His | Arg | Leu | Ala |
|---|---|---|---|---|---|---|---|---|---|---|---|---|---|---|---|
| | | | 35 | | | | 40 | | | | | 45 | | | |

| Thr | Asp | Thr | Ala | Met | Asp | Phe | Phe | Ala | Asn | Gly | Thr | Glu | Ala | Glu | Lys |
|---|---|---|---|---|---|---|---|---|---|---|---|---|---|---|---|
| | 50 | | | | | 55 | | | | | 60 | | | | |

| Ala | Ala | Val | Thr | Thr | Asp | Val | Pro | Thr | Met | Arg | Arg | Gly | Tyr | Ser | Ala |
|---|---|---|---|---|---|---|---|---|---|---|---|---|---|---|---|
| 65 | | | | | 70 | | | | | 75 | | | | | 80 |

| Leu | Glu | Ala | Glu | Ser | Thr | Ala | Gln | Val | Thr | Arg | Thr | Gly | Ser | Tyr | Thr |
|---|---|---|---|---|---|---|---|---|---|---|---|---|---|---|---|
| | | | | 85 | | | | | 90 | | | | | 95 | |

| Asp | Tyr | Ser | Met | Ser | Phe | Ser | Met | Gly | Ile | Ser | Gly | Asn | Val | Phe | Pro |
|---|---|---|---|---|---|---|---|---|---|---|---|---|---|---|---|
| | | | 100 | | | | | 105 | | | | | 110 | | |

| Ser | Pro | Glu | Phe | Glu | Arg | Val | Trp | Thr | Glu | Tyr | Phe | Asp | Lys | Leu | Tyr |
|---|---|---|---|---|---|---|---|---|---|---|---|---|---|---|---|
| | | 115 | | | | | 120 | | | | | 125 | | | |

| Ala | Ala | Ala | Gln | Glu | Thr | Ala | Arg | Leu | Val | Leu | Thr | Ala | Ser | Gly | Gly |
|---|---|---|---|---|---|---|---|---|---|---|---|---|---|---|---|
| | 130 | | | | | 135 | | | | | 140 | | | | |

| Tyr | Asp | Ala | Glu | Ile | Val | Gly | Ser | Leu | Asp | Glu | Leu | Leu | Asp | Ala | Asp |
|---|---|---|---|---|---|---|---|---|---|---|---|---|---|---|---|
| 145 | | | | | 150 | | | | | 155 | | | | | 160 |

| Pro | Val | Leu | Arg | Leu | Arg | Tyr | Phe | Pro | Glu | Val | Pro | Glu | His | Arg | Ser |
|---|---|---|---|---|---|---|---|---|---|---|---|---|---|---|---|
| | | | | 165 | | | | | 170 | | | | | 175 | |

| Ala | Glu | His | Glu | Pro | Asp | Arg | Met | Ala | Pro | His | Tyr | Asp | Leu | Ser | Ile |
|---|---|---|---|---|---|---|---|---|---|---|---|---|---|---|---|
| | | | 180 | | | | | 185 | | | | | 190 | | |

| Ile | Thr | Phe | Ile | His | Gln | Thr | Pro | Cys | Ala | Asn | Gly | Phe | Val | Ser | Leu |
|---|---|---|---|---|---|---|---|---|---|---|---|---|---|---|---|
| | | | 195 | | | | | 200 | | | | | 205 | | |

| Gln | Ala | Glu | Ile | Gly | Gly | Glu | Leu | Val | Ser | Leu | Pro | Val | Val | Glu | Asp |
|---|---|---|---|---|---|---|---|---|---|---|---|---|---|---|---|
| | 210 | | | | | 215 | | | | | 220 | | | | |

| Ala | Val | Val | Val | Met | Cys | Gly | Ala | Met | Ala | Pro | Leu | Ala | Thr | Gln | Gly |
|---|---|---|---|---|---|---|---|---|---|---|---|---|---|---|---|
| 225 | | | | | 230 | | | | | 235 | | | | | 240 |

| Ala | Leu | Pro | Ala | Pro | Arg | His | His | Val | Arg | Ser | Pro | Gly | Ala | Gly | Met |
|---|---|---|---|---|---|---|---|---|---|---|---|---|---|---|---|
| | | | | 245 | | | | | 250 | | | | | 255 | |

| Arg | Glu | Gly | Ser | Asp | Arg | Thr | Ser | Ser | Val | Phe | Phe | Leu | Arg | Pro | Arg |
|---|---|---|---|---|---|---|---|---|---|---|---|---|---|---|---|
| | | | 260 | | | | | 265 | | | | | 270 | | |

| Thr | Asp | Phe | Ser | Phe | Ser | Val | Ala | Lys | Ala | Arg | Ser | Tyr | Gly | Leu | Ala |
|---|---|---|---|---|---|---|---|---|---|---|---|---|---|---|---|
| | | 275 | | | | | 280 | | | | | 285 | | | |

| Val | Asp | Leu | Asp | Met | Glu | Thr | Ala | Thr | Phe | Gly | Asp | Trp | Ile | Gly | Thr |
|---|---|---|---|---|---|---|---|---|---|---|---|---|---|---|---|
| | 290 | | | | | 295 | | | | | 300 | | | | |

| Asn | Tyr | Val | Thr | Met | His | Ala | Lys | Asn | Glu | Pro | Gln | Ala | Gly |
|---|---|---|---|---|---|---|---|---|---|---|---|---|---|
| 305 | | | | | 310 | | | | | 315 | | | |

<210> SEQ ID NO 12
<211> LENGTH: 2852
<212> TYPE: DNA
<213> ORGANISM: Artificial Sequence
<220> FEATURE:
<223> OTHER INFORMATION: PK Plasmid

<400> SEQUENCE: 12

```
gatctcgatc ccgcgaaatt aatacgactc actataggga gaccacaacg gtttccctct     60
agaaataatt ttgtttaact ttaagaagga gatatacata tgcggggttc tcatcatcat    120
```

```
catcatcatg gtatggctag catgactggt ggacagcaaa tgggtcggga tctgtacgac      180
gatgacgata aggatcgatg gggatccgag ctcgagatct gcagctggta ccatggaatt      240
cgaagcttga tccggctgct aacaaagccc gaaaggaagc tgagttggct gctgccaccg      300
ctgagcaata actagcataa ccccttgggg cctctaaacg gtcttgaggg gttttttgc       360 tgaaaggagg aactatatcc ggatctggcg taatagcgaa gaggcccgca ccgatcgccc      420
ttcccaacag ttgcgcagcc tgaatggcga atgggacgcg ccctgtagcg gcgcattaag      480
cgcggcgggt gtggtggtta cgcgcagcgt gaccgctaca cttgccagcg ccctagcgcc      540
cgctcctttc gctttcttcc cttcctttct cgccacgttc gccggctttc cccgtcaagc      600
tctaaatcgg gggctccctt tagggttccg atttagtgct ttacggcacc tcgaccccaa      660
aaaacttgat tagggtgatg gttcacgtag tgggccatcg ccctgataga cggtttttcg      720
ccctttgacg ttggagtcca cgttctttaa tagtggactc ttgttccaaa ctggaacaac      780 actcaacccct atcgcggtct attcttttga tttataaggg attttgccga tttcggccta    840
ttggttaaaa aatgagctga tttaacaaat atttaacgcg aattttaaca aaatattaac     900
gcttacaatt taggtggcac ttttcgggga aatgtgcgcg gaacccctat ttgtttattt     960
ttctaaatac attcaaatat gtatccgctc atgagacaat aaccctgata aatgcttcaa     1020
taatattgaa aaaggaagag tatgagtcat attcaacggg aaacgtcttg ctctaggccg     1080
cgattaaatt ccaacatgga tgctgattta tatgggtata aatgggctcg cgataatgtc     1140
gggcaatcag gtgcgacaat ctatcgattg tatgggaagc ccgatgcgcc agagttgttt     1200
ctgaaacatg gcaaaggtag cgttgccaat gatgttacag atgagatggt cagactaaac     1260
tggctgacgg aatttatgcc tcttccgacc atcaagcatt ttatccgtac tcctgatgat     1320
gcatggttac tcaccactgc gatccccggg aaaacagcat tccaggtatt agaagaatat     1380
cctgattcag gtgaaaatat tgttgatgcg ctggcagtgt tcctgcgccg gttgcattcg     1440
attcctgttt gtaattgtcc ttttaacagc gatcgcgtat ttcgtctcgc tcaggcgcaa     1500
tcacgaatga ataacggttt ggttgatgcg agtgattttg atgacgagcg taatggctgg     1560
cctgttgaac aagtctggaa agaaatgcat aaacttttgc cattctcacc ggattcagtc     1620
gtcactcatg gtgatttctc acttgataac cttattttg acgaggggaa attaataggt      1680
tgtattgatg ttggacgagt cggaatcgca gaccgatacc aggatcttgc catcctatgg     1740
aactgcctcg gtgagttttc tccttcatta cagaaacggc ttttttcaaaa atatggtatt    1800 gataatcctg atatgaataa attgcagttt catttgatgc tcgatgagtt tttctaactg     1860
tcagaccaag tttactcata tatactttag attgatttaa aacttcattt ttaatttaaa     1920
aggatctagg tgaagatcct ttttgataat ctcatgacca aaatccctta acgtgagttt     1980
tcgttccact gagcgtcaga ccccgtagaa aagatcaaag gatcttcttg agatccttt      2040 tttctgcgcg taatctgctg cttgcaaaca aaaaaaccac cgctaccagc ggtggtttgt     2100
ttgccggatc aagagctacc aactcttttt ccgaaggtaa ctggcttcag cagagcgcag     2160
ataccaaata ctgtccttct agtgtagccg tagttaggcc accacttcaa gaactctgta     2220
gcaccgccta catacctcgc tctgctaatc ctgttaccag tggctgctgc cagtggcgat     2280
aagtcgtgtc ttaccgggtt ggactcaaga cgatagttac cggataaggc gcagcggtcg     2340
ggctgaacgg ggggttcgtg cacacagccc agcttggagc gaacgaccta caccgaactg     2400
agatacctac agcgtgagct atgagaaagc gccacgcttc ccgaagggag aaaggcggac     2460
aggtatccgg taagcggcag ggtcggaaca ggagagcgca cgagggagct tccaggggga     2520
```

-continued

```
aacgcctggt atctttatag tcctgtcggg tttcgccacc tctgacttga gcgtcgattt      2580
ttgtgatgct cgtcaggggg gcggagccta tggaaaaacg ccagcaacgc ggccttttta      2640
cggttcctgg gcttttgctg gccttttgct cacatgttct ttcctgcgtt atcccctgat      2700
tctgtggata accgtattac cgcctttgag tgagctgata ccgctcgccg cagccgaacg      2760
accgagcgca gcgagtcagt gagcgaggaa gcggaagagc gcccaatacg caaaccgcct      2820
ctccccgcgc gttggccgat tcattaatgc ag                                    2852

<210> SEQ ID NO 13
<211> LENGTH: 33
<212> TYPE: DNA
<213> ORGANISM: Artificial Sequence
<220> FEATURE:
<223> OTHER INFORMATION: PR Frgment Forward Primer

<400> SEQUENCE: 13
ctgtcagacc aagtttactc atatatactt tag                                   33

<210> SEQ ID NO 14
<211> LENGTH: 28
<212> TYPE: DNA
<213> ORGANISM: Artificial Sequence
<220> FEATURE:
<223> OTHER INFORMATION: PR Fragment Reverse Primer

<400> SEQUENCE: 14
actcttcctt tttcaatatt attgaagc                                         28

<210> SEQ ID NO 15
<211> LENGTH: 23
<212> TYPE: DNA
<213> ORGANISM: Artificial Sequence
<220> FEATURE:
<223> OTHER INFORMATION: KAN Fragment Forward Primer

<400> SEQUENCE: 15
atgagtcata ttcaacggga aac                                              23

<210> SEQ ID NO 16
<211> LENGTH: 27
<212> TYPE: DNA
<213> ORGANISM: Artificial Sequence
<220> FEATURE:
<223> OTHER INFORMATION: KAN Fragment Reverse Primer

<400> SEQUENCE: 16
ttagaaaaac tcatcgagca tcaaatg                                          27

<210> SEQ ID NO 17
<211> LENGTH: 25
<212> TYPE: DNA
<213> ORGANISM: Artificial Sequence
<220> FEATURE:
<223> OTHER INFORMATION: Wild-Type Forward Primer

<400> SEQUENCE: 17
gtcatatggc agataccccg gtgcc                                            25

<210> SEQ ID NO 18
<211> LENGTH: 29
<212> TYPE: DNA
<213> ORGANISM: Artificial Sequence
<220> FEATURE:
```

<223> OTHER INFORMATION: Wild-Type Reverse Primer

<400> SEQUENCE: 18
gctagatctt tagcccgcct gcggttcat                                29

<210> SEQ ID NO 19
<211> LENGTH: 31
<212> TYPE: DNA
<213> ORGANISM: Artificial Sequence
<220> FEATURE:
<223> OTHER INFORMATION: HD-G29H Forward Primer

<400> SEQUENCE: 19
gaatgtgtga cccacatggg tgttttctat c                             31

<210> SEQ ID NO 20
<211> LENGTH: 31
<212> TYPE: DNA
<213> ORGANISM: Artificial Sequence
<220> FEATURE:
<223> OTHER INFORMATION: HD-G29H Reverse Primer

<400> SEQUENCE: 20
gatagaaaac acccatgtgg gtcacacatt c                             31

<210> SEQ ID NO 21
<211> LENGTH: 24
<212> TYPE: DNA
<213> ORGANISM: Artificial Sequence
<220> FEATURE:
<223> OTHER INFORMATION: HD-A40L Forwrd Primer

<400> SEQUENCE: 21
ggctacggtc tgggcgataa agac                                     24

<210> SEQ ID NO 22
<211> LENGTH: 24
<212> TYPE: DNA
<213> ORGANISM: Artificial Sequence
<220> FEATURE:
<223> OTHER INFORMATION: HD-A40L Reverse Primer

<400> SEQUENCE: 22
gtctttatcg cccagaccgt agcc                                     24

<210> SEQ ID NO 23
<211> LENGTH: 26
<212> TYPE: DNA
<213> ORGANISM: Artificial Sequence
<220> FEATURE:
<223> OTHER INFORMATION: HD-G41T Forward Primer

<400> SEQUENCE: 23
gctacggtgc aaccgataaa gaccac                                   26

<210> SEQ ID NO 24
<211> LENGTH: 26
<212> TYPE: DNA
<213> ORGANISM: Artificial Sequence
<220> FEATURE:
<223> OTHER INFORMATION: HD-G41T Reverse Primer

<400> SEQUENCE: 24
gtggtctttt tcggttgcac cgtagc                                   26

```
<210> SEQ ID NO 25
<211> LENGTH: 23
<212> TYPE: DNA
<213> ORGANISM: Artificial Sequence
<220> FEATURE:
<223> OTHER INFORMATION: HD-R182D Forward Primer

<400> SEQUENCE: 25
gaacacgaac cggatcgtat ggc                                              23

<210> SEQ ID NO 26
<211> LENGTH: 23
<212> TYPE: DNA
<213> ORGANISM: Artificial Sequence
<220> FEATURE:
<223> OTHER INFORMATION: HD-R182D Reverse Primer

<400> SEQUENCE: 26
gccatacgat ccggttcgtg ttc                                              23

<210> SEQ ID NO 27
<211> LENGTH: 21
<212> TYPE: DNA
<213> ORGANISM: Artificial Sequence
<220> FEATURE:
<223> OTHER INFORMATION: HD-T272R Forwrd Primer

<400> SEQUENCE: 27
gcgtccgcgt accgactttt c                                                21

<210> SEQ ID NO 28
<211> LENGTH: 21
<212> TYPE: DNA
<213> ORGANISM: Artificial Sequence
<220> FEATURE:
<223> OTHER INFORMATION: HD-T272R Reverse Primer

<400> SEQUENCE: 28
gaaaagtcgg tacgcggacg c                                                21
```

DEACETOXYCEPHALOSPORIN C HYDROXYLASE MUTANTS, DNA ENCODING THE MUTANTS, METHOD FOR UTILIZING THE MUTANTS AND APPLICATION THEREOF

This application is the United States national phase of International Application No. PCT/CN2017/086843 filed Jun. 1, 2017, and claims priority to Chinese Patent Application No. 201610516090.9 filed Jul. 1, 2016, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1806394—ST25.txt. The size of the text file is 36,755 bytes, and the text file was created on Dec. 12, 2018.

FIELD OF THE INVENTION

The present invention relates to genetic modification and protein engineering, which involves deacetoxycephalosporin C hydroxylase mutants, their encoding DNA sequences and the methods to utilize them and their application.

BACKGROUND OF THE INVENTION

Deacetyl-7-aminocephalosporanic acid (D-7-ACA) (formula 1) is a precursor of β-lactam antibiotics cephalosporins. The current method of synthesis is to use 7-aminocephalosporanic acid (7-ACA) (formula 2) as substrate. D-7-ACA can also be synthesized from enzymatic reaction using phenylacetyl deacetyl-7-aminocephalosporanic acid (G-D-7-ACA) (formula 3) and phenylacetyl-7-aminodeacetoxycephalosporanic acid (G-7-ADCA) (formula 4) as substrates. The enzymes involved are deacetoxycephalosporin C hydroxylase and penicillin G acylase.

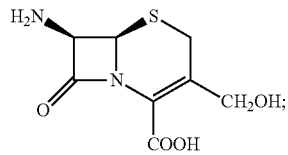

(Formula 1)

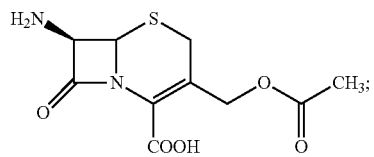

(Formula 2)

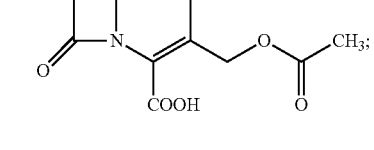

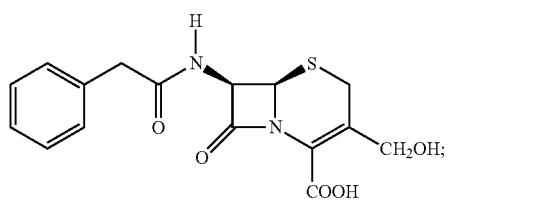

(Formula 3)

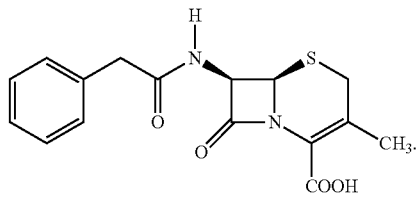

(Formula 4)

Currently, the enzymatic activity of deacetoxycephalosporin C hydroxylase for the relatively low-cost substrate G-7-ADCA is quite low (WO 2008/107782; 445/CHE/2009, Coque, J. J. R., et al; Appl. Microbiol. Biotechnol. 44, 605-609, 1996; EP465189; U.S. Pat. No. 6,180,361). Therefore, scientists are working to improve its activity (WO2013/105030).

At this moment, there are still requirement to improve the thermostability and activity to G-7-ADCA of the deacetoxycephalosporin C hydroxylase.

DESCRIPTION OF THE INVENTION

In this invention, Deacetoxycephalosporin C hydroxylase mutants, DNA encoding the mutants, method for utilizing the mutants and application thereof are provided for possible solution for the above mentioned technical problems.

In details, this invention provides:

(1) A deacetoxycephalosporin C hydroxylase mutant characterized by at least one amino acid mutation at residue position selected from Glycine at position 29, Alanine at position 40, Glycine at position 41, Arginine at position 182 and Threonine at position 272, based on amino acid sequence shown in SEQ ID NO.:2 as reference sequence, and wherein the deacetoxycephalosporin C hydroxylase mutant has at least 10% increase in the activity towards G-7-ADCA and at least 150% increase in thermostability compared to wild-type deacetoxycephalosporin C hydroxylase.

(2) The deacetoxycephalosporin C hydroxylase mutant according to (1), characterized by substitution of Glycine at position 29 by Histidine.

(3) The deacetoxycephalosporin C hydroxylase mutant according to (1), characterized by substitution of Alanine at position 40 by Leucine.

(4) The deacetoxycephalosporin C hydroxylase mutant according to (1), characterized by substitution of Glycine at position 41 by Threonine.

(5) The deacetoxycephalosporin C hydroxylase mutant according to (1), characterized by substitution of Arginine at position 182 by Aspartic Acid.

(6) The deacetoxycephalosporin C hydroxylase mutant according to (1), characterized by substitution of Threonine at position 272 by Arginine.

(7) The deacetoxycephalosporin C hydroxylase mutant according to (1), characterized by mutations of Glycine at position 29 and Glycine at position 41.

(8) The deacetoxycephalosporin C hydroxylase mutant according to (7), characterized by substitutions of Glycine at position 29 by Histidine and Glycine at position 41 by Threonine.

(9) The deacetoxycephalosporin C hydroxylase mutant according to (1), characterized by mutations of Glycine at position 29, Glycine at position 41 and Threonine at position 272.

(10) The deacetoxycephalosporin C hydroxylase mutant according to (9), characterized by substitutions of Glycine at position 29 by Histidine, Glycine at position 41 by Threonine and Threonine at position 272 by Arginine.

(11) The deacetoxycephalosporin C hydroxylase mutant according to (1), characterized by mutations of Glycine at position 29, Alanine at position 40, Glycine at position 41 and Threonine at position 272.

(12) The deacetoxycephalosporin C hydroxylase mutant according to (11), characterized by substitutions of Glycine at position 29 by Histidine, Alanine at position 40 by Leucine, Glycine at position 41 by Threonine and Threonine at position 272 by Arginine.

(13) The deacetoxycephalosporin C hydroxylase mutant according to (1), characterized by mutations of Glycine at position 29, Alanine at position 40, Glycine at position 41, Arginine at position 182 and Threonine at position 272.

(14) The deacetoxycephalosporin C hydroxylase mutant according to (13), characterized by substitutions of Glycine at position 29 by Histidine, Alanine at position 40 by Leucine, Glycine at position 41 by Threonine, Arginine at position 182 by Aspartic acid and Threonine at position 272 by Arginine.

(15) An isolated DNA comprising the nucleotide sequence encoding the deacetoxycephalosporin C hydroxylase mutant according to any one of (1)-(14).

(16) The use of deacetoxycephalosporin C hydroxylase mutant according to any one of 1-14 in the phenylacetyl deacetyl-7-aminocephalosporanic acid (G-D-7-ACA) synthesis using phenylacetyl-7-aminodeacetoxycephalosporanic acid (G-7-ADCA) as substrate.

(17) The use of deacetoxycephalosporin C hydroxylase mutant according to any one of 1-14 in the Deacetyl-7-aminocephalosporanic acid (D-7-ACA) synthesis using phenylacetyl-7-aminodeacetoxycephalosporanic acid (G-7-ADCA) as substrate.

(18) The use of deacetoxycephalosporin C hydroxylase mutant according to any one of 1-14 in the 7-aminocephalosporanic acid (7-ACA) synthesis using phenylacetyl-7-aminodeacetoxycephalosporanic acid (G-7-ADCA) as substrate.

(19) A method for the preparation of phenylacetyl deacetyl-7-aminocephalosporanic acid (G-D-7-ACA), comprising making the deacetoxycephalosporin C hydroxylase mutant according to any one of 1-14 to react with phenylacetyl-7-aminodeacetoxycephalosporanic acid (G-7-ADCA).

(20) A method for the preparation of Deacetyl-7-aminocephalosporanic acid (D-7-ACA), comprising making the deacetoxycephalosporin C hydroxylase mutant according to any one of 1-14 to react with phenylacetyl-7-aminodeacetoxycephalosporanic acid (G-7-ADCA).

(21) A method for the preparation of 7-aminocephalosporanic acid (7-ACA), comprising making the deacetoxycephalosporin C hydroxylase mutant according to any one of 1-14 to react with phenylacetyl-7-aminodeacetoxycephalosporanic acid (G-7-ADCA).

The present invention has the following advantages and positive effects when compared to the prior art:

This invention genetically modified deacetoxycephalosporin C hydroxylase from *Streptomyces clavuligerus* and thereby increased its thermostability and activity towards G-7-ADCA. Compared to wild-type, the enzymatic activity of the deacetoxycephalosporin C hydroxylase of this invention has increased at least 10% and its thermostability has increased at least 150%, thus allowing it to be more commercially and industrially viable.

DETAILS DESCRIPTION OF THE INVENTION

This invention is further explained, but not limited to, in the following description. As long as the basic principles of this invention are followed, any changes and modifications are included in this invention.

In order to answer the aforementioned technical difficulties, this invention went through in depth study of theories and experimental testing. With the help from genetic and protein engineering, this invention modified deacetoxycephalosporin C hydroxylase from *Streptomyces clavuligerus* and produced a series of its mutants with increased activity and thermostability which highly benefits the production of G-D-7-ACA.

Specifically, this invention provides a deacetoxycephalosporin C hydroxylase mutant characterized by at least one amino acid mutation at residue position selected from Glycine at position 29, Alanine at position 40, Glycine at position 41, Arginine at position 182 and Threonine at position 272, based on amino acid sequence shown in SEQ ID NO.:2 as reference sequence, and wherein the deacetoxycephalosporin C hydroxylase mutant has at least 10% increase in the activity and at least 150% increase in thermostability compared to wild-type deacetoxycephalosporin C hydroxylase.

Preferably, the Glycine at position 29 is substituted by Histidine.

Preferably, the Alanine at position 40 is substituted by Leucine.

Preferably, the Glycine at position 41 is substituted by Threonine.

Preferably, the Arginine at position 182 is substituted by Aspartic Acid.

Preferably, the Threonine at position 272 is substituted by Arginine.

Preferably, the deacetoxycephalosporin C hydroxylase mutants contain both mutations for Glycine at position 29 and Glycine at position 41. More preferably, the aforementioned Glycine at position 29 is substituted by Histidine and Glycine at position 41 is substituted by Threonine.

Furthermore, the deacetoxycephalosporin C hydroxylase mutant preferably contains mutations for Glycine at position 29, Glycine at position 41 and Threonine at position 272. More preferably, the aforementioned Glycine at position 29 is substituted by Histidine, Glycine at position 41 is substituted by Threonine and Threonine at position 272 is substituted by Arginine.

By preference, the deacetoxycephalosporin C hydroxylase mutant contains mutations for Glycine at position 29, Alanine at position 40, Glycine at position 41 and Threonine at position 272. More preferably, the aforementioned Glycine at position 29 is substituted by Histidine, Alanine at position 40 is substituted by Leucine, Glycine at position 41 is substituted by Threonine and Threonine at position 272 is substituted by Arginine.

Ideally, the deacetoxycephalosporin C hydroxylase mutant contains mutations for Glycine at position 29, Alanine at position 40, Glycine at position 41, Arginine at position 182 and Threonine at position 272. More ideally, the aforementioned Glycine at position 29 is substituted by Histidine, Alanine at position 40 is substituted by Leucine, Glycine at position 41 is substituted by Threonine, Arginine at position 182 is substituted by Aspartic Acid and Threonine at position 272 is substituted by Arginine.

By preference, the deacetoxycephalosporin C hydroxylase mutants in this invention have amino acid sequence represented by SEQ ID NO.: 3 in the sequence list. In another preferred embodiment of the invention, the deacetoxycephalosporin C hydroxylase mutants in this invention have amino acid sequence represented by SEQ ID NO.: 4 in the sequence list. In yet another preferred embodiment of the invention, the deacetoxycephalosporin C hydroxylase mutants in this invention have amino acid sequence represented by SEQ ID NO.: 5 in the sequence list. In further another preferred embodiment of the invention, the deacetoxycephalosporin C hydroxylase mutants in this invention have amino acid sequence represented by SEQ ID NO.: 6 in the sequence list. In further another preferred embodiment of the invention, the deacetoxycephalosporin C hydroxylase mutants in this invention have amino acid sequence represented by SEQ ID NO.: 7 in the sequence list. In further another preferred embodiment of the invention, the deacetoxycephalosporin C hydroxylase mutants in this invention have amino acid sequence represented by SEQ ID NO.: 8 in the sequence list. In further another preferred embodiment of the invention, the deacetoxycephalosporin C hydroxylase mutants in this invention have amino acid sequence represented by SEQ ID NO.: 9 in the sequence list. In further another preferred embodiment of the invention, the deacetoxycephalosporin C hydroxylase mutants in this invention have amino acid sequence represented by SEQ ID NO.: 10 in the sequence list. In further another preferred embodiment of the invention, the deacetoxycephalosporin C hydroxylase mutants in this invention have amino acid sequence represented by SEQ ID NO.: 11 in the sequence list.

The deacetoxycephalosporin C hydroxylase mutants can be obtained through directed mutagenesis of wild-type *Streptomyces clavuligerus* deacetoxycephalosporin C hydroxylase using already known genetic modification and cloning techniques. The DNA sequence of aforementioned wild-type *Streptomyces clavuligerus* deacetoxycephalosporin C hydroxylase is represented by SEQ ID NO.: 1 in the sequence list and its amino acid sequence is represented by SEQ ID NO.: 2.

The cloning techniques and protocols used are as follows for example: The desired point mutation was first located on the amino acid sequence of wild-type deacetoxycephalosporin C hydroxylase. The plasmid containing wild-type deacetoxycephalosporin C hydroxylase gene was then modified by PCR amplification using primers that contained the altered DNA sequence corresponding to the desired mutation. The DNA fragments containing the desired point mutation were amplified by PCR to produce a full-length deacetoxycephalosporin C hydroxylase gene with the point mutation. The mutated deacetoxycephalosporin C hydroxylase gene was ligated to an appropriate vector and transformed into a suitable host. The transformed hosts were incubated and screened for having higher deacetoxycephalosporin C hydroxylase activity and thermostability. Finally, the plasmid DNA were extracted and its sequence was analysed to ensure the correct mutations were introduced into the deacetoxycephalosporin C hydroxylase gene.

The DNA recombination methods in this invention can use any appropriate vectors. For example, appropriate vectors include but not limited to prokaryotic expression vectors such as pRSET and pET21; eukaryotic expression vectors such as pYD1 and pYES2/GS; cloning vectors such as pGEMT-Easy, pUC18/19 and pBluscript-SK.

The mutated deacetoxycephalosporin C hydroxylase genes created by the DNA recombination methods in this invention can be expressed using any known expression methods in this field within or without prokaryotic and eukaryotic hosts.

The host cells utilized by the DNA recombination methods in this invention can be prokaryotic or eukaryotic cells. The aforementioned prokaryotic hosts include but not limited to *Escherichia coli*, *Bacillus coagulans*, *Bacillus subtilis*, *Bacillus megaterium*, *Thermoanaerobacterium saccharolyticum* and *Streptomyces*. The aforementioned eukaryotic hosts include but not limited to *Saccharomyces cerevisiae* and *Pichia pastoris*.

The term "reference sequence" used in the present invention refers to the sequence in SEQ ID NO.:1 when it is a nucleotide sequence, and refers to the sequence in SEQ ID NO.:2 when it is an amino acid sequence.

The deacetoxycephalosporin C hydroxylase enzyme mutants in this invention can be utilized in unpurified form, as well as partially purified or purified form, in addition to immobilized enzymes/immobilized cells.

The deacetoxycephalosporin C hydroxylase mutants in this invention can have at least one amino acid difference compared to the amino acid sequence shown in SEQ ID NO.:2 in the sequence list. Additionally, the mutants' enzymatic activity have at least 10% increase compared to wild-type deacetoxycephalosporin C hydroxylase, preferably at least 10%-100% increase, more preferably at least 250% increase, and/or the thermostability have at least 150% increase compared to wild-type deacetoxycephalosporin C hydroxylase, preferably at least 900% increase, more preferably 2400% increase. By preference, the mutants have at least one mutation compared to the amino acid sequence shown in SEQ ID NO.:2 as reference sequence: Glycine (Gly) at position 29 is substituted by Histidine (His), Alanine (Ala) at position 40 is substituted by Leucine (Leu), Glycine (Gly) at position 41 is substituted by Threonine (Thr), Arginine (Arg) at position 182 is substituted by Aspartic Acid (Asp) and Threonine (Thr) at position 272 is substituted by Arginine (Arg).

This invention also provides a DNA which comprises the nucleotide sequence of aforementioned deacetoxycephalosporin C hydroxylase mutant.

This invention also provides the use of deacetoxycephalosporin C hydroxylase mutant according to the present invention in the phenylacetyl deacetyl-7-aminocephalosporanic acid (G-D-7-ACA) synthesis using phenylacetyl-7-aminodeacetoxycephalosporanic acid (G-7-ADCA) as substrate.

This invention also provides the use of deacetoxycephalosporin C hydroxylase mutant according to the present invention in the deacetyl-7-aminocephalosporanic acid (D-7-ACA) synthesis using phenylacetyl-7-aminodeacetoxycephalosporanic acid (G-7-ADCA) as substrate.

This invention also provides the use of deacetoxycephalosporin C hydroxylase mutant according to the present invention in the 7-aminocephalosporanic acid (7-ACA) synthesis using phenylacetyl-7-aminodeacetoxycephalosporanic acid (G-7-ADCA) as substrate.

The production of G-D-7-ACA, D-7-ACA and 7-ACA can use any commonly known methods in this field of application, as long as the deacetoxycephalosporin C hydroxylase mutants mentioned in this invention are used in the corresponding step within the protocols.

This invention also provides a method for the preparation of G-D-7-ACA, which includes reacting the aforementioned deacetoxycephalosporin C hydroxylase mutants with G-7-ADCA. The person skilled in the art can understand that this method can also use other reactants and materials required in G-D-7-ACA production.

This invention also provides a method for the preparation of D-7-ACA, which includes reacting the aforementioned deacetoxycephalosporin C hydroxylase mutants with G-7-ADCA. The person skilled in the art can understand that this method can also use other reactants and materials required in D-7-ACA production.

This invention also provides a method for the preparation of 7-ACA, which includes reacting the aforementioned deacetoxycephalosporin C hydroxylase mutants with G-7-ADCA. The person skilled in the art can understand that this method can also use other reactants and materials required in 7-ACA production.

The following section uses examples to further explain this invention, however, these examples should not be interpreted as protection limits of this invention.

EXAMPLES

Any unspecified conditions should follow common protocols or conditions from materials providers. Unless specified, volume/volume % (v/v %) should be used as the percentage of contents.

Example 1: Construction of PK Vector

In order to remove the ampicillin resistance gene from pRSET-A vector (Invitrogen), VF and VR primers (table 1) were designed based on pRSET-A sequence.

In order to obtain the kanamycin resistance gene from pET-28b vector (Novogen), KF and KR primers (table 1) were designed based on the kanamycin resistance gene sequence of pET-28b.

Specifically, DNA fragment PR was amplified using primers VF and VR and the pRSET-A plasmid as template. DNA fragment KAN was amplified using primers KF and KR and the pET-28b plasmid as template.

PCR amplification conditions for PR are as follows: 1 μg of plasmid pRSET-A, 0.1 μg of primers (VF+VR), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols for PR are as follows: 96° C. for 5 mins, 30 cycles of: 94° C. for 45 sec, 53° C. for 45 sec and 72° C. for 3 mins, 72° C. for 10 mins at the end.

After 1% (w/v) agarose gel electrophoresis, a 2036 bp PCR product of PR was extracted and purified using E.Z.N.A. Gel Extraction Kit (Omega Bio-tek Inc.).

PCR amplification conditions for KAN are as follows: 1 μg of plasmid pET-28b, 0.1 μg of primers (KF+KR), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols for KAN are as follows: 96° C. for 5 mins, 30 cycles of: 94° C. for 45 sec, 53° C. for 45 sec and 72° C. for 3 mins, 72° C. for 10 mins at the end. After 1% (w/v) agarose gel electrophoresis, a 816 bp PCR product of KAN was extracted and purified using E.Z.N.A. Gel Extraction Kit (Omega Bio-tek Inc.).

Both PR and KAN DNA fragments were ligated using T4 DNA ligase (NEB) and plasmid PK was obtained. The plasmid was transformed into E. coli BL21 competent cells (Novagen). The transformed cells were incubated on LB plates with 50 mg/L kanamycin at 37° C. PK plasmids were obtained from single colony and extracted using DNA-spin plasmid DNA purification kit (Intron Biotechnology). The correct sequence was confirmed with DNA sequencing (sequence list SEQ ID NO.:12).

Example 2: Deacetoxycephalosporin C Hydroxylase Gene Cloning and Construction of pGEMT-Hd Plasmid The deacetoxycephalosporin C hydroxylase gene DNA sequence was obtained from DNA sequence database (GenBank: M63809). The DNA sequence was optimised according to host cell codon usage bias using software Gene Designer 2.0. Primers HF and HR (table 1) were designed based on the gene sequence.

The aforementioned DNA sequence was synthesized and plasmid Hd-pUC was obtained (synthesized and ligated to vector pUC57 by GenScript corp.). A 957 bp PCR amplification product was obtained using HF and HR as primers and plasmid Hd-pUC as template.

PCR amplification conditions are as follows: 1 μg of plasmid Hd-pUC, 0.1 μg of primers (HF+HR), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols are as follows: 96° C. for 5 mins, 30 cycles of: 94° C. for 45 sec, 53° C. for 45 sec and 72° C. for 3 mins, 72° C. for 10 mins at the end.

The amplified wild-type deacetoxycephalosporin C hydroxylase gene DNA were purified with 1% (w/v) agarose gel electrophoresis, a 957 bp PCR product of hd was extracted and purified using E.Z.N.A. Gel Extraction Kit (Omega Bio-tek Inc.). The fragment was ligated to pGEMT-Easy (Promega) using T4 ligase (NEB) through TA cloning to create plasmid pGEMT-hd. The plasmid was transformed into E. coli BL21 competent cells (Novagen). The transformed cells were incubated on LB plates with 50 mg/L ampicillin at 37° C. pGEMT-hd plasmids were obtained from single colony and extracted using DNA-spin plasmid DNA purification kit (Intron Biotechnology). The correct sequence was confirmed with DNA sequencing.

Example 3: Amino Acid Site-Directed Mutagenesis of Deacetoxycephalosporin C Hydroxylase at Position 41

"PCR Protocols (John M. S. Bartlett and David Stirling. Totowa, N.J.: Humana Press, 2003)" was used as reference for site-directed mutagenesis techniques.

The plasmid pGEMT-hd (example 2) was used as template to design primers 41TF and 41TR (table 1). The Glycine (Gly) at position 41 in the original amino acid sequence was substituted into Threonine (Thr), to create mutant HD-G41T.

Specifically, DNA fragment 41T1 was amplified using primers HF and 41TR and plasmid pGEMT-hd as template. DNA fragment 41T2 was amplified using primers 41TF and HR. PCR amplification conditions are as follows: 1 μg of plasmid pGEMT-hd, 0.1 μg of primers (HF+41TR) (for fragment 41T1 amplification), or 0.1 μg of primers (41TF+HR) (for fragment 41T2 amplification), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols are as follows: 96° C. for 5 mins, 30 cycles of: 94° C. for 45 sec, 53° C. for 45 sec and 72° C. for 60 sec, 72° C. for 10 mins at the end. The amplified 41T1 and 41T2 DNA fragments were purified with 1% (w/v) agarose gel electrophoresis and were extracted and purified using E.Z.N.A. Gel Extraction Kit (Omega Bio-tek Inc.), and then were used to amplify the full-length gene using primers HF and HR. PCR amplification conditions are as follows: 50 ng of DNA fragment 41T1 and 50 ng of DNA fragment 41T2, 0.1 μg of primers (HF+HR), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols are as follows: 96° C. for 5 mins, 30 cycles of: 94° C. for 45 sec, 53° C. for 45 sec and 72° C. for 2 mins, 72° C. for 10 mins at the end.

The full length mutated gene was purified with 1% (w/v) agarose gel electrophoresis, extracted and purified using E.Z.N.A. Gel Extraction Kit (Omega Bio-tek Inc.) to obtain a 957 bp full-length mutated gene HD-G41T.

Mutants HD-G29H, HD-A40L, HD-R182D and HD-T272R were constructed using similar methods mentioned above, with primers referred in table 1.

Example 4: Construction of Plasmid PK-HD-G41T

The mutant DNA HD-G41T and the vector PK were digested by restriction enzymes NdeI+BglII (NEB) and purified by DNA gel electrophoresis in 1% (w/v) agarose gel. The restriction enzyme digested products were extracted and purified using E.Z.N.A. Gel Extraction Kit (Omega Bio-tek Inc.). They were ligated using T4 ligase (NEB) and transformed into *E. coli* HB101 competent cells (Bio-Rad). The transformed cells were incubated on LB plates with 50 mg/L kanamycin at 37° C. PK-HD-G41T plasmids were obtained from single colony and extracted using DNA-spin plasmid DNA purification kit (Intron Biotechnology). The correct sequence was confirmed with DNA sequencing.

The plasmids PK-HD-G29H, PK-HD-A40L, PK-HD-R182D and PK-HD-T272R were constructed using similar methods mentioned above.

Example 5: Construction of Deacetoxycephalosporin C Hydroxylase Plasmid PK-HD-29H41T with Two Mutations Combination "PCR Protocols (John M. S. Bartlett and David Stirling. Totowa, N.J.: Humana Press, 2003)" was used as reference for site-directed mutagenesis techniques.

The plasmid PK-HD-G41T (example 4) was used as template to perform substitution of Glycine (Gly) at position 29 with Histidine (His), to create mutant HD-29H41T.

Specifically, PK-HD-G41T was used as template to amplify fragment 29H41T1 using primers HF and 29HR, and fragment 29H41T2 using primers 29HF and HR. PCR amplification conditions are as follows: 1 μg of plasmid PK-HD-G41T, 0.1 μg of primers (HF+29HR) (for fragment 29H41T1 amplification), or 0.1 μg of primers (29HF+HR) (for fragment 29H41T2 amplification), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols are as follows: 96° C. for 5 mins, 30 cycles of: 94° C. for 45 sec, 53° C. for 45 sec and 72° C. for 60 sec, 72° C. for 10 mins at the end.

The amplified 29H41T1 and 29H41T2 DNA fragments were purified with 1% (w/v) agarose gel electrophoresis and were extracted and purified using E.Z.N.A. Gel Extraction Kit (Omega Bio-tek Inc.), and then were used to amplify the full-length gene using primers HF and HR. PCR amplification conditions are as follows: 50 ng of DNA fragment 29H41T1 and 50 ng of DNA fragment 29H41T2, 0.1 μg of primers (HF+HR), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols are as follows: 96° C. for 5 mins, 30 cycles of: 94° C. for 45 sec, 53° C. for 45 sec and 72° C. for 2 mins, 72° C. for 10 mins at the end.

The amplified full length mutated gene were purified with 1% (w/v) agarose gel electrophoresis, extracted and purified using E.Z.N.A. Gel Extraction Kit (Omega Bio-tek Inc.) to obtain a 957 bp full-length mutated gene HD-29H41T.

NdeI and BglII (NEB) were used to digest the mutant gene HD-29H41T and vector PK. The digested products were purified by 1% (w/v) agarose gel electrophoresis, extracted and purified using E.Z.N.A. Gel Extraction Kit (Omega Bio-tek Inc.). Ligated using T4 ligase (NEB) and transformed into *E. coli* HB101 competent cells (Bio-Rad). The transformed cells were incubated on LB plates with 50 mg/L kanamycin at 37° C. PK-HD-29H41T plasmids were obtained from single colony and extracted using DNA-spin plasmid DNA purification kit (Intron Biotechnology). The correct sequence was confirmed with DNA sequencing.

Example 6: Construction of Deacetoxycephalosporin C Hydroxylase Plasmid PK-HD-Sp3 with Three Mutations Combination "PCR Protocols (John M. S. Bartlett and David Stirling. Totowa, N.J.: Humana Press, 2003)" was used as reference for site-directed mutagenesis techniques.

The plasmid PK-HD-29H41T (example 5) was used as template to perform substitution of Threonine (Thr) at position 272 with Arginine (Arg), to create mutant HD-sp3.

Specifically, PK-HD-29H41T was used as template to amplify fragment sp3-1 using primers HF and 272RR, and fragment sp3-2 using primers 272RF and HR. PCR amplification conditions are as follows: 1 μg of plasmid PK-HD-29H41T, 0.1 μg of primers (HF+272RR) (for fragment sp3-1 amplification), or 0.1 μg of primers (272RF+HR) (for fragment sp3-2 amplification), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols are as follows: 96° C. for 5 mins, 30 cycles of: 94° C. for 45 sec, 53° C. for 45 sec and 72° C. for 60 sec, 72° C. for 10 mins at the end.

The amplified sp3-1 and sp3-2 DNA fragments were purified with 1% (w/v) agarose gel electrophoresis and were extracted and purified using E.Z.N.A. Gel Extraction Kit (Omega Bio-tek Inc.), and then were used to amplify the full-length gene using primers HF and HR. PCR amplification conditions are as follows: 50 ng of DNA fragment sp3-1 and 50 ng of DNA fragment sp3-2, 0.1 μg of primers (HF+HR), 5 μl of 10× buffer (200 mM Tris-HCl (pH 8.0), 100 mM KCl, 100 mM (NH4)2SO4, 20 mM MgSO4, 1% Triton X-100), 4% DMSO, 4 μl of 2.5 mM dNTP, 1 U of LA Taq DNA polymerase (TaKaRa), sterilized water to make up to 50 μl reaction.

PCR amplification protocols are as follows: 96° C. for 5 mins, 30 cycles of: 94° C. for 45 sec, 53° C. for 45 sec and 72° C. for 2 mins, 72° C. for 10 mins at the end.

The amplified full length mutated gene were purified with 1% (w/v) agarose gel electrophoresis, extracted and purified using E.Z.N.A. Gel Extraction Kit (Omega Bio-tek Inc.) to obtain a 957 bp full-length mutated gene HD-sp3.

NdeI and BglII were used to digest the mutant gene HD-sp3 and the vector PK. The digested products were purified by 1% (w/v) agarose gel electrophoresis, extracted and purified using E.Z.N.A. Gel Extraction Kit (Omega Bio-tek Inc.). Ligated using T4 ligase (NEB) and transformed into *E. coli* HB101 competent cells (Biorad). The transformed cells were incubated on LB plates with 50 mg/L kanamycin at 37° C. PK-HD-sp3 plasmids were obtained from single colony and extracted using DNA-spin plasmid DNA purification kit (Intron Biotechnology). The correct sequence was confirmed with DNA sequencing.

Example 7: Construction of Deacetoxycephalosporin C Hydroxylase Plasmid PK-HD-Sp4 with Four Mutations Combination "PCR Protocols (John M. S. Bartlett and David Stirling. Totowa, N.J.: Humana Press, 2003)" was used as reference for site-directed mutagenesis techniques.

The plasmid PK-HD-sp3 (example 6) was used as template to perform substitution of Alanine (Ala) at position 40 with Leucine (Leu), to create mutant HD-sp4.

Specifically, PK-HD-sp3 was used as template to amplify fragment sp4-1 using primers HF and 40LR, and fragment sp4-2 using primers 40LF and HR. PCR amplification conditions are as follows: 1 µg of plasmid PK-HD-sp3, 0.1 µg of primers (HF+40LR) (for fragment sp4-1 amplification), or 0.1 µg of primers (40LF+HR) (for fragment sp4-2 amplification), 5 µl of 10× buffer (200 mM Tris-HCl (pH 8.0), 100 mM KCl, 100 mM (NH4)2SO4, 20 mM MgSO4, 1% Triton X-100), 4% DMSO, 4 µl of 2.5 mM dNTP, 1 U of LA Taq DNA polymerase (TaKaRa), sterilized water to make up to 50 µl reaction.

PCR amplification protocols are as follows: 96° C. for 5 mins, 30 cycles of: 94° C. for 45 sec, 53° C. for 45 sec and 72° C. for 60 sec, 72° C. for 10 mins at the end.

The amplified sp4-1 and sp4-2 DNA fragments were purified with 1% (w/v) agarose gel electrophoresis and were extracted and purified using E.Z.N.A. Gel Extraction Kit (Omega Bio-tek Inc.), and then were used to amplify the full-length gene using primers HF and HR. PCR amplification conditions are as follows: 50 ng of DNA fragment sp4-1 and 50 ng of DNA fragment sp4-2, 0.1 µg of primers (HF+HR), 5 µl of 10× buffer (200 mM Tris-HCl (pH 8.0), 100 mM KCl, 100 mM (NH4)2SO4, 20 mM MgSO4, 1% Triton X-100), 4% DMSO, 4 µl of 2.5 mM dNTP, 1 U of LA Taq DNA polymerase (TaKaRa), sterilized water to make up to 50 µl reaction.

PCR amplification protocols are as follows: 96° C. for 5 mins, 30 cycles of: 94° C. for 45 sec, 53° C. for 45 sec and 72° C. for 2 mins, 72° C. for 10 mins at the end.

The full length mutated gene were purified with 1% (w/v) agarose gel electrophoresis, extracted and purified using E.Z.N.A. Gel Extraction Kit (Omega Bio-tek Inc.) to obtain a 957 bp full-length mutated gene HD-sp4.

NdeI and BglII were used to digest the mutant gene HD-sp4 and vector PK. The digested products were purified by 1% (w/v) agarose gel electrophoresis, extracted and purified using E.Z.N.A. Gel Extraction Kit (Omega Bio-tek Inc.). Ligated using T4 ligase (NEB) and transformed into *E. coli* HB101 competent cells (Biorad). The transformed cells were incubated on LB plates with 50 mg/L kanamycin at 37° C. PK-HD-sp4 plasmids were obtained from single colony and extracted using DNA-spin plasmid DNA purification kit (Intron Biotechnology). The correct sequence was confirmed with DNA sequencing.

Example 8: Construction of Deacetoxycephalosporin C Hydroxylase Plasmid PK-HD-Sp5 with Five Mutations Combination "PCR Protocols (John M. S. Bartlett and David Stirling. Totowa, N.J.: Humana Press, 2003)" was used as reference for site-directed mutagenesis techniques.

The plasmid PK-HD-sp4 (example 7) was used as template to perform substitution of Arginine (Arg) at position 182 with Aspartic acid (Asp), to create mutant HD-sp5.

Specifically, PK-HD-sp4 was used as template to amplify fragment sp5-1 using primers HF and 182DR, and fragment sp5-2 using primers 182DF and HR. PCR amplification conditions are as follows: 1 µg of plasmid PK-HD-sp4, 0.1 µg of primers (HF+182DR) (for fragment sp5-1 amplification), or 0.1 µg of primers (182DF+HR) (for fragment sp5-2 amplification), 5 µl of 10× buffer (200 mM Tris-HCl (pH 8.0), 100 mM KCl, 100 mM (NH4)2SO4, 20 mM MgSO4, 1% Triton X-100), 4% DMSO, 4 µl of 2.5 mM dNTP, 1 U of LA Taq DNA polymerase (TaKaRa), sterilized water to make up to 50 µl reaction.

PCR amplification protocols are as follows: 96° C. for 5 mins, 30 cycles of: 94° C. for 45 sec, 53° C. for 45 sec and 72° C. for 60 sec, 72° C. for 10 mins at the end.

The amplified sp5-1 and sp5-2 DNA fragments were purified with 1% (w/v) agarose gel electrophoresis and were extracted and purified using E.Z.N.A. Gel Extraction Kit (Omega Bio-tek Inc.), and then were used to amplify the full-length gene using primers HF and HR. PCR amplification conditions are as follows: 50 ng of DNA fragment sp5-1 and 50 ng of DNA fragment sp5-2, 0.1 µg of primers (HF+HR), 5 µl of 10× buffer (200 mM Tris-HCl (pH 8.0), 100 mM KCl, 100 mM (NH4)2SO4, 20 mM MgSO4, 1% Triton X-100), 4% DMSO, 4 µl of 2.5 mM dNTP, 1 U of LA Taq DNA polymerase (TaKaRa), sterilized water to make up to 50 µl reaction.

PCR amplification protocols are as follows: 96° C. for 5 mins, 30 cycles of: 94° C. for 45 sec, 53° C. for 45 sec and 72° C. for 2 mins, 72° C. for 10 mins at the end.

The full length mutated gene were purified with 1% (w/v) agarose gel electrophoresis, extracted and purified using E.Z.N.A. Gel Extraction Kit (Omega Bio-tek Inc.) to obtain a 957 bp full-length mutated gene HD-sp5.

NdeI and BglII (NEB) were used to digest the mutant gene HD-sp5 and vector PK. The digested products were purified by 1% (w/v) agarose gel electrophoresis, extracted and purified using E.Z.N.A. Gel Extraction Kit (Omega Bio-tek Inc.). Ligated using T4 ligase (NEB) and transformed into *E. coli* HB101 competent cells (Biorad). The transformed cells were incubated on LB plates with 50 mg/L kanamycin at 37° C. PK-HD-sp5 plasmids were obtained from single colony and extracted using DNA-spin plasmid DNA purification kit (Intron Biotechnology). The correct sequence was confirmed with DNA sequencing.

Example 9: Deacetoxycephalosporin C Hydroxylase Enzymatic Activity Assay

The wild-type deacetoxycephalosporin C hydroxylase plasmid and various deacetoxycephalosporin C hydroxylase mutants plasmids mentioned above were transformed into *E. coli* BL21 (Novagen), respectively, and incubated on LB plates with 50 mg/L kanamycin at 37° C. The transformed cells from single colony were inoculated to 3 ml LB broth with 50 mg/L kanamycin and incubated at 37° C., 250 rpm for 8 hours, followed by taking 1 ml and inoculated to 50 ml LB broth with 50 mg/L kanamycin and incubated at 37° C., 250 rpm for 18 hours. The cells were centrifuged and resuspended in 10 mM pH 7.4 sodium phosphate buffer, followed by cell sonication (50W) lysis with sonication time for 5 sec, 30 times. Cell debris was removed by centrifugation and supernatant were collected as liquid enzyme. The liquid enzyme was tested for deacetoxycephalosporin C hydroxylase enzymatic activity and for enzyme expression by SDS-PAGE. The following are the details:

900 μl of substrate (10 mM G-7-ADCA, 20 mM sodium α-ketoglutarate, 4 mM sodium L-ascorbate and 1.8 mM ferrous sulfate heptahydrate, 6 mM sodium phosphate buffer (pH 7.5)) were added to 1.5 ml eppendorf tube, followed by adding 100 μl of the above mentioned liquid enzyme. The reaction solution was mixed well and shaken at 200 rpm in a thermoshaker at 30° C. for 30 mins. 10 μl supernatant was taken and added into 990 μl H2O, mixed, followed by UPLC analysis for G-D-7ACA concentration and the enzymatic activity was calculated. The activities of wild-type deacetoxycephalosporin C hydroxylase and various deacetoxycephalosporin C hydroxylase mutants were compared as shown in table 2.

UPLC analysis conditions were as follows: Acquity UPLC column: Acquity UPLC BEH C18 column (Waters Corporation, 1.7 μm, guard column: 2.1 mm×5 mm, column: 2.1 mm×50 mm); mobile phase: (A) 50 mM KH2PO4/K2HPO4 (pH 7.0), 6% acetonitrile, (B) 60% acetonitrile; column temperature: 40° C.; flowrate: 0.3 ml/min; detection wavelength: 260 nm.

Example 10: Deacetoxycephalosporin C Hydroxylase Thermostability Assay

Liquid enzymes of wild-type deacetoxycephalosporin C hydroxylase and the various deacetoxycephalosporin C hydroxylase mutants were prepared according to example 9. 200 μl liquid enzymes were added into 1.5 ml eppendorf tubes and were placed in 42° C. water bath for 10 mins of heat treatment. The samples were centrifuged and supernatant were collected for enzymatic activity assay according to example 9. The remaining enzymatic activity of wild-type deacetoxycephalosporin C hydroxylase and of various deacetoxycephalosporin C hydroxylase mutants were calculated by dividing activity of heat treated deacetoxycephalosporin C hydroxylase by activity of untreated deacetoxycephalosporin C hydroxylase and presented it as percentage. The percentage of increased enzyme thermostability was calculated by the following formula. Table 3 in the following indicated the remaining enzymatic activity of wild-type and various deacetoxycephalosporin C hydroxylase mutants after heat treatment.

$$A=(B-C)/C\times100\%=(B-2\%)/2\%\times100\%$$

Where:
A—Percentage of increased thermostability
B—The remaining activity of deacetoxycephalosporin C hydroxylase mutant after the heat treatment
C—the remaining activity of wild-type after the heat treatment

Example 11: G-D-7-ACA Production Using G-7-ADCA as Substrate

Substrate was prepared with the following final concentration of components: 10 mM G-7-ADCA, 20 mM sodium α-ketoglutarate, 4 mM sodium L-ascorbate and 1.8 mM ferrous sulfate heptahydrate were dissolved in 90 ml 6 mM pH 7.4 sodium phosphate buffer. 1M NaOH was used to adjust the pH to 6, followed by adding 10 ml liquid enzyme. The reaction was placed on magnetic stir plate and stirred at high speed. The reaction was maintained at 30° C. and pH 6.4 for 150 mins. 1 ml sample was taken at 30, 60, 90, 120 and 150 mins from the reaction. The reaction samples were centrifuged at 13000 rpm for 1 min and 10 μl supernatant was taken and added into 990 μl H2O, mixed, followed by UPLC analysis for G-D-7ACA concentration.

UPLC analysis conditions were as follows: Acquity UPLC column: Acquity UPLC BEH C18 column (Waters Corporation, 1.7 μm, guard column: 2.1 mm×5 mm, column: 2.1 mm×50 mm); mobile phase: (A) 50 mM KH2PO4/K2HPO4 (pH 7.0), 6% acetonitrile, (B) 60% acetonitrile; column temperature: 40° C.; flow rate: 0.3 ml/min; detection wavelength: 260 nm.

This invention is not limited by the detailed description provided in the text above. Various modifications can be made and these modifications should also be regarded as being within the scope of the invention, which is defined by the claims.

TABLE 1

| Products Name | Primers Sequence | |
|---|---|---|
| PR Fragment | VF: 5' | CTGTCAGACCAAGTTTACTCATATATACTTTAG 3' (SEQ ID NO.: 13) |
|  | VR: 5' | ACTCTTCCTTTTTCAATATTATTGAAGC 3' (SEQ ID NO.: 14) |
| KAN Fragment | KF: 5' | ATGAGTCATATTCAACGGGAAAC 3' (SEQ ID NO.: 15) |
|  | KR: 5' | TTAGAAAAACTCATCGAGCATCAAATG 3' (SEQ ID NO.: 16) |
| Wild-Type | HF: 5' | GTCATATGGCAGATACCCCGGTGCC 3' (SEQ ID NO.: 17) |
|  | HR: 5' | GCTAGATCTTTAGCCCGCCTGCGGTTCAT 3' (SEQ ID NO.: 18) |
| mutant HD-G29H | 29HF: 5' | GAATGTGTGACCCACATGGGTGTTTTCTATC 3' (SEQ ID NO.: 19) |
|  | 29HR: 5' | GATAGAAAACACCCATGTGGGTCACACATTC 3' (SEQ ID NO.: 20) |
| mutant HD-A40L | 40LF: 5' | GGCTACGGTCTGGGCGATAAAGAC 3' (SEQ ID NO.: 21) |
|  | 40LR: 5' | GTCTTTATCGCCCAGACCGTAGCC 3' (SEQ ID NO.: 22) |
| mutant HD-G41T | 41TF: 5' | GCTACGGTGCAACCGATAAAGACCAC 3' (SEQ ID NO.: 23) |
|  | 41TR: 5' | GTGGTCTTTATCGGTTGCACCGTAGC 3' (SEQ ID NO.: 24) |

TABLE 1-continued

```
Products
Name        Primers Sequence mutant      182DF: 5' GAACACGAACCGGATCGTATGGC 3' (SEQ ID NO.: 25)
HD-R182D    182DR: 5' GCCATACGATCCGGTTCGTGTTC 3' (SEQ ID NO.: 26)

mutant      272RF: 5' GCGTCCGCGTACCGACTTTTC 3'   (SEQ ID NO.: 27)
HD-T272R    272RR: 5' GAAAAGTCGGTACGCGGACGC 3'   (SEQ ID NO.: 28)
```

TABLE 2

The comparison of wild-type and mutated deacetoxycephalosporin C hydroxylase enzymatic activity

| Sequence List Number | Enzyme Name | Enzymatic Activity (%) |
|---|---|---|
| SEQ ID NO.: 2 | Wild-Type | 100 |
| SEQ ID NO.: 3 | HD-G29H | 110 |
| SEQ ID NO.: 4 | HD-A40L | 120 |
| SEQ ID NO.: 5 | HD-G41T | 160 |
| SEQ ID NO.: 6 | HD-R182D | 140 |
| SEQ ID NO.: 7 | HD-T272R | 150 |
| SEQ ID NO.: 8 | HD-29H41T | 180 |
| SEQ ID NO.: 9 | Sp3 | 200 |
| SEQ ID NO.: 10 | Sp4 | 220 |
| SEQ ID NO.: 11 | Sp5 | 250 |

TABLE 3

Thermostability of mutants

| Enzyme Name | Remaining Activity after Heat Treatment at 42° C. for 10 min (%) | Increased Thermostability (%) |
|---|---|---|
| Wild-Type | 2 | — |
| HD-G29H | 5 | 150 |
| HD-A40L | 20 | 900 |
| HD-G41T | 10 | 400 |
| HD-R182D | 12 | 500 |
| HD-T272R | 15 | 650 |
| HD-29H41T | 25 | 1150 |
| Sp3 | 40 | 1900 |
| Sp4 | 45 | 2150 |
| Sp5 | 50 | 2400 |

The invention claimed is:

1. A deacetoxycephalosporin C hydroxylase mutant of wild-type deacetoxycephalosporin C hydroxylase of SEQ ID NO: 2, wherein the mutation of the mutant is selected from the group consisting of G29H, A4OL, G41T, R182D, T272R, G29HG41T, G29H-G41T-T272R, G29H-A40L-G41T-T272R and G29H-A40L-G41T-R182D-T272R substitutions, and wherein the deacetoxycephalosporin C hydroxylase mutant has at least 10% increase in activity and at least 150% increase in thermostability compared to wild-type deacetoxycephalosporin C hydroxylase.

2. The deacetoxycephalosporin C hydroxylase mutant according to claim 1, wherein the mutation is a substitution of Glycine at position 29 by Histidine.

3. The deacetoxycephalosporin C hydroxylase mutant according to claim 1, wherein the mutation is a substitution of Alanine at position 40 by Leucine.

4. The deacetoxycephalosporin C hydroxylase mutant according to claim 1, wherein the mutation is a substitution of Glycine at position 41 by Threonine.

5. The deacetoxycephalosporin C hydroxylase mutant according to claim 1, wherein the mutation is a substitution of Arginine at position 182 by Aspartic Acid.

6. The deacetoxycephalosporin C hydroxylase mutant according to claim 1, wherein the mutation is a substitution of Threonine at position 272 by Arginine.

7. The deacetoxycephalosporin C hydroxylase mutant according to claim 1, wherein the mutation is substitutions of Glycine at position 29 by Histidine, and Glycine at position 41 by Threonine.

8. The deacetoxycephalosporin C hydroxylase mutant according to claim 1, wherein the mutation is substitutions of Glycine at position 29 by Histidine, Glycine at position 41 by Threonine, and Threonine at position 272 by Arginine.

9. The deacetoxycephalosporin C hydroxylase mutant according to claim 1, wherein the mutation is substitutions of Glycine at position 29 by Histidine, Alanine at position 40 by Leucine, Glycine at position 41 by Threonine, and Threonine at position 272 by Arginine.

10. The deacetoxycephalosporin C hydroxylase mutant according to claim 1, wherein the mutation is substitutions of Glycine at position 29 by Histidine, Alanine at position 40 by Leucine, Glycine at position 41 by Threonine, Arginine at position 182 by Aspartic acid, and Threonine at position 272 by Arginine.

11. An isolated DNA comprising a nucleotide sequence encoding the deacetoxycephalosporin C hydroxylase mutant according to claim 1.

12. A method for the preparation of phenylacetyl deacetyl-7-aminocephalosporanic acid (G-D-7-ACA), comprising causing the deacetoxycephalosporin C hydroxylase mutant according to claim 1 to react with phenylacetyl-7-aminodeacetoxycephalosporanic acid (G-7-ADCA).

13. A method for the preparation of deacetyl-7-aminocephalosporanic acid (D-7-ACA), comprising causing the deacetoxycephalosporin C hydroxylase mutant according to claim 1 to react with phenylacetyl-7-aminodeacetoxycephalosporanic acid (G-7-ADCA).

14. A method for the preparation of 7-aminocephalosporanic acid (7-ACA), comprising causing the deacetoxycephalosporin C hydroxylase mutant according to claim 1 to react with phenylacetyl-7-aminodeacetoxycephalosporanic acid (G-7-ADCA).

* * * * *